(12) United States Patent
Lai et al.

(10) Patent No.: US 7,763,261 B2
(45) Date of Patent: Jul. 27, 2010

(54) ANTI-HUMAN CYTOMEGALOVIRUS ANTIBODIES

(75) Inventors: Jiann-Shiun Lai, Xizhi (TW);
Chi-Kuan Chen, Xizhi (TW);
Young-Sun Lin, Xizhi (TW);
Chao-Yang Huang, Xizhi (TW)

(73) Assignee: DCB-USA LLC, Wilmington, DE (US)

( * ) Notice: Subject to any disclaimer, the term of this patent is extended or adjusted under 35 U.S.C. 154(b) by 0 days.

(21) Appl. No.: 12/259,014

(22) Filed: Oct. 27, 2008

(65) Prior Publication Data

US 2009/0162378 A1 Jun. 25, 2009

Related U.S. Application Data

(60) Provisional application No. 61/014,945, filed on Dec. 19, 2007.

(51) Int. Cl.
*A61K 39/245* (2006.01)
(52) U.S. Cl. .................. 424/230.1; 424/130.1
(58) Field of Classification Search .......... None
See application file for complete search history.

(56) References Cited

U.S. PATENT DOCUMENTS

| 5,043,281 | A | 8/1991 | Masuho |
| 5,750,106 | A | 5/1998 | Ostberg |
| 6,569,616 | B1 | 5/2003 | Compton |
| 7,147,861 | B2 | 12/2006 | Compton |
| 2004/0166544 | A1* | 8/2004 | Morton et al. ............. 435/7.23 |

FOREIGN PATENT DOCUMENTS

| JP | 7067631 | 3/1995 |

OTHER PUBLICATIONS

Boeckh, et al., "Randomized, Placebo-Controlled, Double-Blind Study of a Cytomegalovirus-Specific Monoclonal Antibody (MSL-109) for Prevention of Cytomegalovirus Infection After Allogeneic Hematopoietic Stem Cell Transplantation", Biology of Blood and Marrow Transplantation. vol. 7(6), pp. 343-351(2001).

Böldicke, et al., "Human Monoclonal Antibodies to Cytomegalovirus Characterization and Recombinant Expression of a Glycoprotein-B-Specific Antibody", European Journal of Biochemistry. vol. 234(2), pp. 397-405 (Dec. 1, 1995).

Furebring, et al., "Antibody-Mediated Neutralization of Cytomegalovirus: Modulation of Efficacy Induced Through the IgG Constant Region", Molecular Immunology. vol. 38(11), pp. 833-840 (2001).

Marshall, et al., "Antibodies to the Major Linear Neutralizing Domains of Cytomegalovirus Glycoprotein B Among Natural Seropositives and CMV Subunit Vaccine Recipients", Viral Immunology vol. 13(3), pp. 329-341 (2000).

Rasmussen, et al., "Neutralizing Antibody to gB2 Human Cytomegalovirus Does not Prevent Reactivation in Patients with Human Immunodeficiency Virus Infection", Journal of General Virology. vol. 84(Pt. 7), pp. 1853-1857 (Jul. 2003).

Wang, et al., "Recombinant Modified Vaccinia Virus Ankara Expressing a Soluble Form of Glycoprotein B Causes Durable Immunity and Neutralizing Antibodies Against Multiple Strains of Human Cytomegalovirus", Journal of Virology, vol. 78(8), pp. 3965-3976 (Apr. 2004).

\* cited by examiner

*Primary Examiner*—Ali R. Salimi
(74) *Attorney, Agent, or Firm*—Occhiuti Rohlicek & Tsao LLP

(57) ABSTRACT

The present invention features a human antibody that specifically binds to human cytomegalovirus (HCMV), its encoding nucleic acid(s), and use of the antibody/nucleic acid(s) in treating HCMV infection.

12 Claims, No Drawings

SEQUENCE LISTING

```
<160> NUMBER OF SEQ ID NOS: 40

<210> SEQ ID NO 1
<211> LENGTH: 120
<212> TYPE: PRT
<213> ORGANISM: Homo sapiens

<400> SEQUENCE: 1

Met Ala Gln Val Gln Leu Gln Glu Ser Gly Pro Gly Leu Val Lys Pro
1               5                   10                  15

Ser Gly Thr Leu Ser Leu Thr Cys Ala Val Ser Gly Gly Ser Ile Ser
            20                  25                  30

Ser Ser Asn Trp Trp Ser Trp Val Arg Gln Pro Pro Gly Lys Gly Leu
        35                  40                  45
```

```
Glu Trp Ile Gly Glu Ile Tyr His Ser Gly Ser Thr Asn Tyr Asn Pro
    50                  55                  60

Ser Leu Lys Ser Arg Val Thr Ile Ser Val Asp Lys Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Glu Gly Ser Tyr Glu Ala Phe Asp Tyr Trp Gly Gln
            100                 105                 110

Gly Thr Leu Val Thr Val Ser Ser
            115                 120

<210> SEQ ID NO 2
<211> LENGTH: 115
<212> TYPE: PRT
<213> ORGANISM: Homo sapiens

<400> SEQUENCE: 2

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
                20                  25                  30

Tyr Val Gln Trp Tyr Gln Gln Arg Pro Gly Ser Ala Pro Ser Thr Val
            35                  40                  45

Ile Tyr Asp Asp Asn Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Gly Val Val Phe Gly Gly Gly Thr Lys Leu Thr Val Leu
            100                 105                 110

Gly Ala Ala
        115

<210> SEQ ID NO 3
<211> LENGTH: 250
<212> TYPE: PRT
<213> ORGANISM: Artificial
<220> FEATURE:
<223> OTHER INFORMATION: single-chain antibody

<400> SEQUENCE: 3

Met Ala Gln Val Gln Leu Gln Glu Ser Gly Pro Gly Leu Val Lys Pro
1               5                   10                  15

Ser Gly Thr Leu Ser Leu Thr Cys Ala Val Ser Gly Gly Ser Ile Ser
                20                  25                  30

Ser Ser Asn Trp Trp Ser Trp Val Arg Gln Pro Pro Gly Lys Gly Leu
            35                  40                  45

Glu Trp Ile Gly Glu Ile Tyr His Ser Gly Ser Thr Asn Tyr Asn Pro
        50                  55                  60

Ser Leu Lys Ser Arg Val Thr Ile Ser Val Asp Lys Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Glu Gly Ser Tyr Glu Ala Phe Asp Tyr Trp Gly Gln
            100                 105                 110
```

```
Gly Thr Leu Val Thr Val Ser Ser Gly Gly Gly Ser Gly Gly Gly
        115                 120                 125

Gly Ser Gly Gly Gly Ser Asn Phe Met Leu Thr Gln Pro His Ser
        130                 135                 140

Val Ser Glu Ser Pro Gly Lys Thr Val Thr Ile Ser Cys Thr Arg Ser
145                 150                 155                 160

Ser Gly Ser Ile Ala Ser Asn Tyr Val Gln Trp Tyr Gln Gln Arg Pro
                165                 170                 175

Gly Ser Ala Pro Ser Thr Val Ile Tyr Asp Asp Asn Gln Arg Pro Ser
                180                 185                 190

Gly Val Pro Asp Arg Phe Ser Gly Ser Ile Asp Ser Ser Ser Asn Ser
                195                 200                 205

Ala Ser Leu Thr Ile Ser Gly Leu Lys Thr Glu Asp Glu Ala Asp Tyr
        210                 215                 220

Tyr Cys Gln Ser Tyr Asp Ser Ser Asn His Gly Val Val Phe Gly Gly
225                 230                 235                 240

Gly Thr Lys Leu Thr Val Leu Gly Ala Ala
                245                 250
```

<210> SEQ ID NO 4
<211> LENGTH: 360
<212> TYPE: DNA
<213> ORGANISM: Homo sapiens

<400> SEQUENCE: 4

```
atggcccagg tgcagctgca ggagtcgggc ccaggactgg tgaagccttc ggggaccctg    60
tccctcacct gcgctgtctc tggtggctcc atcagcagta gtaactggtg gagttgggtc   120
cgccagcccc cagggaaggg gctggagtgg attgggaaa  tctatcatag tgggagcacc   180
aactacaacc cgtccctcaa gagtcgagtc accatatcag tagacaagtc caagaaccag   240
ttctccctga agctgagctc tgtgaccgcc gcggacacgg ccgtgtatta ctgtgcgaga   300
gaggggagct acgaggcatt tgactactgg ggccagggaa ccctggtcac cgtctcctca   360
```

<210> SEQ ID NO 5
<211> LENGTH: 339
<212> TYPE: DNA
<213> ORGANISM: Homo sapiens

<400> SEQUENCE: 5

```
aattttatgc tgactcagcc ccactctgtg tcggagtctc cggggaagac ggtaaccatc    60
tcctgcactc gcagcagtgg cagcattgcc agcaactatg tgcagtggta ccagcagcgc   120
ccgggtagtg cccccagcac tgtgatctat gacgataacc aaagaccctc tggggtccct   180
gatcggttct ctggctccat cgacagctcc tccaactctg cctccctcac catctctgga   240
ctgaagactg aggacgaggc tgactactac tgtcagtctt atgatagcag caatcatgga   300
gtggtattcg gcggagggac caagctgacc gtcctaggt                          339
```

<210> SEQ ID NO 6
<211> LENGTH: 744
<212> TYPE: DNA
<213> ORGANISM: Artificial
<220> FEATURE:
<223> OTHER INFORMATION: single-chain antibody gene

<400> SEQUENCE: 6

```
atggcccagg tgcagctgca ggagtcgggc ccaggactgg tgaagccttc ggggaccctg    60
```

-continued

```
tccctcacct gcgctgtctc tggtggctcc atcagcagta gtaactggtg gagttgggtc      120
cgccagcccc cagggaaggg gctggagtgg attggggaaa tctatcatag tgggagcacc      180
aactacaacc cgtccctcaa gagtcgagtc accatatcag tagacaagtc caagaaccag      240
ttctccctga agctgagctc tgtgaccgcc gcggacacgg ccgtgtatta ctgtgcgaga      300 gagggagct acgaggcatt tgactactgg ggcagggaa ccctggtcac cgtctcctca       360
ggtggaggcg gttcaggcgg aggtggctct ggcggtggcg gatcgaattt tatgctgact      420 cagcccact ctgtgtcgga gtctccgggg aagacggtaa ccatctcctg cactcgcagc      480
agtggcagca ttgccagcaa ctatgtgcag tggtaccagc agcgcccggg tagtgccccc      540
agcactgtga tctatgacga taaccaaaga ccctctgggg tccctgatcg gttctctggc      600
tccatcgaca gctcctccaa ctctgcctcc ctcaccatct ctggactgaa gactgaggac      660
gaggctgact actactgtca gtcttatgat agcagcaatc atggagtggt attcggcgga      720
gggaccaagc tgaccgtcct aggt                                             744
```

<210> SEQ ID NO 7
<211> LENGTH: 56
<212> TYPE: DNA
<213> ORGANISM: Artificial
<220> FEATURE:
<223> OTHER INFORMATION: Primer

<400> SEQUENCE: 7

```
gtcctcgcaa ctgcggccca gccggccatg gcccaggtgc agctggtgsa rtctgg        56
```

<210> SEQ ID NO 8
<211> LENGTH: 56
<212> TYPE: DNA
<213> ORGANISM: Artificial
<220> FEATURE:
<223> OTHER INFORMATION: Primer

<400> SEQUENCE: 8

```
gtcctcgcaa ctgcggccca gccggccatg gcccaggtca acttaaggga gtctgg        56
```

<210> SEQ ID NO 9
<211> LENGTH: 54
<212> TYPE: DNA
<213> ORGANISM: Artificial
<220> FEATURE:
<223> OTHER INFORMATION: Primer

<400> SEQUENCE: 9

```
gtcctcgcaa ctgcggccca gccggccatg gccgaggtgc agctgktgga gwcy          54
```

<210> SEQ ID NO 10
<211> LENGTH: 55
<212> TYPE: DNA
<213> ORGANISM: Artificial
<220> FEATURE:
<223> OTHER INFORMATION: Primer

<400> SEQUENCE: 10

```
gtcctcgcaa ctgcggccca gccggccatg gcccaggtgc agctgcagga gtcsg         55
```

<210> SEQ ID NO 11
<211> LENGTH: 56
<212> TYPE: DNA
<213> ORGANISM: Artificial
<220> FEATURE:
<223> OTHER INFORMATION: Primer

```
<400> SEQUENCE: 11
gtcctcgcaa ctgcggccca gccggccatg gccgaggtgc agctgttgca gtctgc         56

<210> SEQ ID NO 12
<211> LENGTH: 54
<212> TYPE: DNA
<213> ORGANISM: Artificial
<220> FEATURE:
<223> OTHER INFORMATION: Primer

<400> SEQUENCE: 12
gtcctcgcaa ctgcggccca gccggccatg gcccaggtac agctgcagca gtca           54

<210> SEQ ID NO 13
<211> LENGTH: 55
<212> TYPE: DNA
<213> ORGANISM: Artificial
<220> FEATURE:
<223> OTHER INFORMATION: Primer

<400> SEQUENCE: 13
gtcctcgcaa ctgcggccca gccggccatg gcccagrtca ccttgaagga gtctg          55

<210> SEQ ID NO 14
<211> LENGTH: 55
<212> TYPE: DNA
<213> ORGANISM: Artificial
<220> FEATURE:
<223> OTHER INFORMATION: Primer

<400> SEQUENCE: 14
gtcctcgcaa ctgcggccca gccggccatg gcccaggtgc agctacagca gtggg          55

<210> SEQ ID NO 15
<211> LENGTH: 24
<212> TYPE: DNA
<213> ORGANISM: Artificial
<220> FEATURE:
<223> OTHER INFORMATION: Primer

<400> SEQUENCE: 15
tgaggagacg gtgaccaggg tgcc                                            24

<210> SEQ ID NO 16
<211> LENGTH: 24
<212> TYPE: DNA
<213> ORGANISM: Artificial
<220> FEATURE:
<223> OTHER INFORMATION: Primer

<400> SEQUENCE: 16
tgaagagacg gtgaccattg tccc                                            24

<210> SEQ ID NO 17
<211> LENGTH: 24
<212> TYPE: DNA
<213> ORGANISM: Artificial
<220> FEATURE:
<223> OTHER INFORMATION: Primer

<400> SEQUENCE: 17
tgaggagacg gtgaccaggg ttcc                                            24

<210> SEQ ID NO 18
```

```
<211> LENGTH: 24
<212> TYPE: DNA
<213> ORGANISM: Artificial
<220> FEATURE:
<223> OTHER INFORMATION: Primer

<400> SEQUENCE: 18
tgaggagacg gtgaccgtgg tccc                                          24

<210> SEQ ID NO 19
<211> LENGTH: 23
<212> TYPE: DNA
<213> ORGANISM: Artificial
<220> FEATURE:
<223> OTHER INFORMATION: Primer

<400> SEQUENCE: 19
gacatccaga tgacccagtc tcc                                           23

<210> SEQ ID NO 20
<211> LENGTH: 23
<212> TYPE: DNA
<213> ORGANISM: Artificial
<220> FEATURE:
<223> OTHER INFORMATION: Primer

<400> SEQUENCE: 20
gatgttgtga tgactcagtc tcc                                           23

<210> SEQ ID NO 21
<211> LENGTH: 23
<212> TYPE: DNA
<213> ORGANISM: Artificial
<220> FEATURE:
<223> OTHER INFORMATION: Primer

<400> SEQUENCE: 21
gaaattgtgt tgacgcagtc tcc                                           23

<210> SEQ ID NO 22
<211> LENGTH: 23
<212> TYPE: DNA
<213> ORGANISM: Artificial
<220> FEATURE:
<223> OTHER INFORMATION: Primer

<400> SEQUENCE: 22
gacatcgtga tgacccagtc tcc                                           23

<210> SEQ ID NO 23
<211> LENGTH: 23
<212> TYPE: DNA
<213> ORGANISM: Artificial
<220> FEATURE:
<223> OTHER INFORMATION: Primer

<400> SEQUENCE: 23
gaaacgacac tcacgcagtc tcc                                           23

<210> SEQ ID NO 24
<211> LENGTH: 23
<212> TYPE: DNA
<213> ORGANISM: Artificial
<220> FEATURE:
<223> OTHER INFORMATION: Primer

<400> SEQUENCE: 24
```

-continued gaaattgtgc tgactcagtc tcc                                        23

<210> SEQ ID NO 25
<211> LENGTH: 48
<212> TYPE: DNA
<213> ORGANISM: Artificial
<220> FEATURE:
<223> OTHER INFORMATION: Primer

<400> SEQUENCE: 25
gagtcattct cgacttgcgg ccgcacgttt gatttccacc ttggtccc             48

<210> SEQ ID NO 26
<211> LENGTH: 48
<212> TYPE: DNA
<213> ORGANISM: Artificial
<220> FEATURE:
<223> OTHER INFORMATION: Primer

<400> SEQUENCE: 26
gagtcattct cgacttgcgg ccgcacgttt gatctccagc ttggtccc             48

<210> SEQ ID NO 27
<211> LENGTH: 48
<212> TYPE: DNA
<213> ORGANISM: Artificial
<220> FEATURE:
<223> OTHER INFORMATION: Primer

<400> SEQUENCE: 27
gagtcattct cgacttgcgg ccgcacgttt gatatccact ttggtccc             48

<210> SEQ ID NO 28
<211> LENGTH: 48
<212> TYPE: DNA
<213> ORGANISM: Artificial
<220> FEATURE:
<223> OTHER INFORMATION: Primer

<400> SEQUENCE: 28
gagtcattct cgacttgcgg ccgcacgttt gatctccacc ttggtccc             48

<210> SEQ ID NO 29
<211> LENGTH: 48
<212> TYPE: DNA
<213> ORGANISM: Artificial
<220> FEATURE:
<223> OTHER INFORMATION: Primer

<400> SEQUENCE: 29
gagtcattct cgacttgcgg ccgcacgttt aatctccagt cgtgtccc             48

<210> SEQ ID NO 30
<211> LENGTH: 23
<212> TYPE: DNA
<213> ORGANISM: Artificial
<220> FEATURE:
<223> OTHER INFORMATION: Primer

<400> SEQUENCE: 30
cagtctgtgt tgacgcagcc gcc                                        23

<210> SEQ ID NO 31
<211> LENGTH: 23
<212> TYPE: DNA

```
<213> ORGANISM: Artificial
<220> FEATURE:
<223> OTHER INFORMATION: Primer

<400> SEQUENCE: 31
cagtctgccc tgactcagcc tgc                                              23

<210> SEQ ID NO 32
<211> LENGTH: 23
<212> TYPE: DNA
<213> ORGANISM: Artificial
<220> FEATURE:
<223> OTHER INFORMATION: Primer

<400> SEQUENCE: 32
tcctatgtgc tgactcagcc acc                                              23

<210> SEQ ID NO 33
<211> LENGTH: 23
<212> TYPE: DNA
<213> ORGANISM: Artificial
<220> FEATURE:
<223> OTHER INFORMATION: Primer

<400> SEQUENCE: 33
tcttctgagc tgactcagga ccc                                              23

<210> SEQ ID NO 34
<211> LENGTH: 23
<212> TYPE: DNA
<213> ORGANISM: Artificial
<220> FEATURE:
<223> OTHER INFORMATION: Primer

<400> SEQUENCE: 34
cacgttatac tgactcaacc gcc                                              23

<210> SEQ ID NO 35
<211> LENGTH: 23
<212> TYPE: DNA
<213> ORGANISM: Artificial
<220> FEATURE:
<223> OTHER INFORMATION: Primer

<400> SEQUENCE: 35
caggctgtgc tcactcagcc gtc                                              23

<210> SEQ ID NO 36
<211> LENGTH: 23
<212> TYPE: DNA
<213> ORGANISM: Artificial
<220> FEATURE:
<223> OTHER INFORMATION: Primer

<400> SEQUENCE: 36
aattttatgc tgactcagcc cca                                              23

<210> SEQ ID NO 37
<211> LENGTH: 48
<212> TYPE: DNA
<213> ORGANISM: Artificial
<220> FEATURE:
<223> OTHER INFORMATION: Primer

<400> SEQUENCE: 37
gagtcattct cgacttgcgg ccgcacctag gacggtgacc ttggtccc                    48
```

```
<210> SEQ ID NO 38
<211> LENGTH: 48
<212> TYPE: DNA
<213> ORGANISM: Artificial
<220> FEATURE:
<223> OTHER INFORMATION: Primer

<400> SEQUENCE: 38
gagtcattct cgacttgcgg ccgcacctag gacggtcagc ttggtccc                    48

<210> SEQ ID NO 39
<211> LENGTH: 48
<212> TYPE: DNA
<213> ORGANISM: Artificial
<220> FEATURE:
<223> OTHER INFORMATION: Primer

<400> SEQUENCE: 39
gagtcattct cgacttgcgg ccgcacctaa aacggtgagc tgggtccc                    48

<210> SEQ ID NO 40
<211> LENGTH: 45
<212> TYPE: DNA
<213> ORGANISM: Artificial
<220> FEATURE:
<223> OTHER INFORMATION: linker sequence

<400> SEQUENCE: 40
ggtggaggcg gttcaggcgg aggtggctct ggcggtggcg gatcg                       45
```

ANTI-HUMAN CYTOMEGALOVIRUS ANTIBODIES

CROSS-REFERENCE TO RELATED APPLICATION

This application claims the benefit of U.S. Provisional Application No. 61/014,945 filed on Dec. 19, 2007, the content of which is hereby incorporated by reference in its entirety.

BACKGROUND OF THE INVENTION

Human cytomegalovirus (HCMV), a member of the herpes virus family, infects people of all age and establishes in its hosts a life-long latent infection. Although causing few symptoms in healthy hosts, HCMV infection can be life-threatening in hosts having a weak immune system, e.g., infants, AIDS patients, leukemia patients, and organ transplant recipients.

At present, there are no satisfactory treatments for HCMV infection. Some anti-HCMV drugs, e.g., ganciclovir and valganciclovir, exhibit serious side effects. Others, e.g., CMV-IGIV (Cytogam), showed inconsistent efficacy. Further, vaccines against CMV infection are still in the research stage. Thus, there is a need for a safer and more effective anti-HCMV drug.

SUMMARY OF THE INVENTION

The present invention is based on the identification of a human anti-HCMV antibody that exhibits unexpectedly high efficiency in neutralizing HCMV.

In one aspect, this invention features an antibody that specifically binds to HCMV. This antibody contains a heavy chain variable region ($V_H$) including an amino acid sequence at least 80% (e.g., 85%, 90%, 95%, or 99%) identical to SEQ ID NO:1, and a light chain variable region ($V_L$) including an amino acid sequence at least 80% (e.g., 85%, 90%, 95%, or 99%) identical to SEQ ID NO:2. As an example, this antibody is a single-chain antibody (scFv) including the amino acid sequence of SEQ ID NO:3.

Another aspect of the present invention relates to a nucleic acid encoding both the above-described $V_H$ and $V_L$ fragments. In one example, this nucleic acid includes a nucleotide sequence (e.g., SEQ ID NO:6) encoding SEQ ID NO:3. Also within the scope of this invention are two nucleic acids, one encoding the $V_H$ fragment and the other encoding the $V_L$ fragment.

The antibody or the nucleic acid(s) of this invention can be mixed with a pharmaceutically acceptable carrier to form a pharmaceutical composition.

In yet another aspect, this invention features a method for treating cytomegalovirus infection by administering to a subject in need thereof an effective amount of either the antibody of this invention or its encoding nucleic acid(s).

The details of one or more embodiments of the invention are set forth in the description below. Other features or advantages of the present invention will be apparent from the following detailed description of several embodiments, and also from the appending claims.

DETAILED DESCRIPTION OF THE INVENTION

Described herein is an anti-HCMV antibody, i.e., HCMV-20, and its functional equivalents. The term "antibody" is meant to include intact antibodies, antibody fragments, e.g., Fab and F(ab')$_2$, and genetically modified antibodies, e.g., scFv antibodies, diabodies, and dual variable domain (DVD) Igs.

HCMV-20 antibody contains a $V_H$ fragment, which or a portion of which has the amino acid sequence of SEQ ID NO: 1; and a $V_L$ fragment, which or a portion of which has the amino acid sequence of SEQ ID NO:2. These two amino acid sequences are shown below:

Amino acid sequence of HCMV-20 $V_H$ fragment (SEQ ID NO: 1)

MAQVQLQESGPGLVKPSGTLSLTCAVS░░░░░░░░░░WVRQPPGKGLEW
IG░░░░░░░░░░░░░░RVTISVDKSKNQFSLKLSSVTAADTAVYYCAR
░░░░░░░WGQGTLVTVSS

Amino acid sequence of HCMV-20 $V_L$ fragment (SEQ ID NO: 2)

NFMLTQPHSVSESPGKTVTISC░░░░░░░░░░░░░░WYQQRPGSAPSTVIY
░░░░░░GVPDRFSGSIDSSSNSASLTISGLKTEDEADYYC░░░░░░░░
░░FGGGTKLTVLGAA

The highlighted regions in the above sequences refer to complementarity-determining regions (CDRs).

A functional equivalent of HCMV-20 refers to an anti-HCMV antibody containing a $V_H$ fragment, which or a portion of which is at least 70% (e.g., 75%) identical to SEQ ID NO: 1, and a $V_L$ fragment, which or a portion of which is at least 70% (e.g., 75%) identical to SEQ ID NO:2.

As used herein, "percent homology" of two amino acid sequences is determined using the algorism described in Karlin and Altschul, *Proc, Natl. Acad. Sci. USA* 87:2264-2268, 1990, modified as described in Karlin and Altschul, *Proc, Natl. Acad. Sci. USA* 5873-5877, 1993. Such an algorism is incorporated into the NBLAST and XBLAST programs of Altschul et al., *J. Mol. Biol.* 215:403-410, 1990. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al., *Nucleic Acids Res.* 25:3389-3402, 1997. When utilizing the BLAST and Gapped BLAST programs, the default parameters of the respective programs (e.g., XBLAST and NBLAST) are used. See www.ncbi.nlm.nih.gov.

The antibody of this invention can contain only the $V_H$ and $V_L$ fragments as described above. In one instance, it is an scFv antibody, in which the $V_H$ and $V_L$ fragments are connected either directly or via a linker, e.g., a peptide linker. As an example, the scFv antibody has an amino acid sequence of:

(SEQ ID NO: 3)
MAQVQLQESGPGLVKPSGTLSLTCAVSGGSISSSNWWSWVRQPPGKGLEW

IGEIYHSGSTNYNPSLKSRVTISVDKSKNQFSLKLSSVTAADTAVYYCAR

EGSYEAFDYWGQGTLVTVSSGGGGSGGGGSGGGGSNFMLTQPHSVSESPG

KTVTISCTRSSGSIASNYVQWYQQRPGSAPSTVIYDDNQRPSGVPDRFSG

SIDSSSNSASLTISGLKTEDEADYYCQSYDSSNHGVVFGGGTKLTVLGA

A.

The antibody can also be a whole immunoglobulin molecule, in which the $V_H$ and $V_L$ fragments are respectively linked to a heavy chain constant region and a light chain constant region of an immunoglobulin, e.g., human IgG1, IgG2a, IgG2b, IgG3, IgG4, IgM, IgE, IgD, IgAa, and IgA2.

Any of the above-described antibodies can be made by genetic engineering. In one example, HCMV-20 is prepared by expressing its $V_H$ (SEQ ID NO: 1) and $V_L$ (SEQ ID NO:2) fragments in host cells from one or two expression vectors containing the following two nucleotide sequences (encoding SEQ ID NOs: 1 and 2):

```
Nucleotide sequence that encodes HCMV-20 V_H
fragment
                                         (SEQ ID NO: 4)
ATGGCCCAGGTGCAGCTGCAGGAGTCGGGCCCAGGACTGGTGAAGCCTTC

GGGGACCCTGTCCCTCACCTGCGCTGTCTCTGGTGGCTCCATCAGCAGTA

GTAACTGGTGGAGTTGGGTCCGCCAGCCCCAGGGAAGGGGCTGGAGTGG

ATTGGGGAAATCTATCATAGTGGGAGCACCAACTACAACCCGTCCCTCAA

GAGTCGAGTCACCATATCAGTAGACAAGTCCAAGAACCAGTTCTCCCTGA

AGCTGAGCTCTGTGACCGCCGCGGACACGGCCGTGTATTACTGTGCGAGA

GAGGGGAGCTACGAGGCATTTGACTACTGGGGCCAGGGAACCCTGGTCAC

CGTCTCCTCA

Nucleotide sequence that encodes HCMV-20 V_L
fragment
                                         (SEQ ID NO: 5)
AATTTTATGCTGACTCAGCCCCACTCTGTGTCGGAGTCTCCGGGGAAGAC

GGTAACCATCTCCTGCACTCGCAGCAGTGGCAGCATTGCCAGCAACTATG

TGCAGTGGTACCAGCAGCGCCCGGGTAGTGCCCCCAGCACTGTGATCTAT

GACGATAACCAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGTCTTATGATAGCAGCAATCATGGA

GTGGTATTCGGCGGAGGGACCAAGCTGACCGTCCTAGGT
```

The $V_H$ and $V_L$ fragments can be made as two separate polypeptides and then refolded together to form an antibody. Alternatively, the two fragments are produced as parts of a single polypeptide, e.g., a polypeptide including the amino acid sequence of SEQ ID NO:3 (encoded by SEQ ID NO:6 shown below).

```
Nucleotide Sequence Encoding HCMV-20 scFv Antibody
                                         (SEQ ID NO: 6)
ATGGCCCAGGTGCAGCTGCAGGAGTCGGGCCCAGGACTGGTGAAGCCTTC

GGGGACCCTGTCCCTCACCTGCGCTGTCTCTGGTGGCTCCATCAGCAGTA

GTAACTGGTGGAGTTGGGTCCGCCAGCCCCAGGGAAGGGGCTGGAGTGG

ATTGGGGAAATCTATCATAGTGGGAGCACCAACTACAACCCGTCCCTCAA

GAGTCGAGTCACCATATCAGTAGACAAGTCCAAGAACCAGTTCTCCCTGA

AGCTGAGCTCTGTGACCGCCGCGGACACGGCCGTGTATTACTGTGCGAGA

GAGGGGAGCTACGAGGCATTTGACTACTGGGGCCAGGGAACCCTGGTCAC

CGTCTCCTCAGGTGGAGGCGGTTCAGGCGGAGGTGGCTCTGGCGGTGGCG

GATCGAATTTTATGCTGACTCAGCCCCACTCTGTGTCGGAGTCTCCGGGG

AAGACGGTAACCATCTCCTGCACTCGCAGCAGTGGCAGCATTGCCAGCAA

CTATGTGCAGTGGTACCAGCAGCGCCCGGGTAGTGCCCCCAGCACTGTGA

TCTATGACGATAACCAAAGACCCTCTGGGGTCCCTGATCGGTTCTCTGGC

TCCATCGACAGCTCCTCCAACTCTGCCTCCCTCACCATCTCTGGACTGAA

GACTGAGGACGAGGCTGACTACTACTGTCAGTCTTATGATAGCAGCAATC

ATGGAGTGGTATTCGGCGGAGGGACCAAGCTGACCGTCCTAGGT
```

In another example, a functional equivalent of HCMV-20 is produced by introducing mutations in SEQ ID NO: 1 and SEQ ID NO:2, preferably, in their frame regions (FRs). It is well known that the CDRs of an antibody determine its antigen specificity. Accordingly, mutations in the FRs of HCMV-20 normally would not affect its binding activity to HCMV, which can be examined using methods known in the art, e.g., ELISA or western-blot analysis.

Both the antibodies described herein and their encoding nucleic acids can be mixed with a pharmaceutically acceptable carrier to form pharmaceutical compositions. An "acceptable carrier" is a carrier compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof.

The present invention also features a method of treating HCMV infection by administering an effective amount of any of the antibodies described herein or its encoding nucleic acid(s) to a subject in need of the treatment, e.g., an infant at risk for congenital CMV infection, an organ transplant recipient, a leukemia patient, or an HIV carrier. The term "treating" as used herein refers to the application or administration of a composition including active agents to a subject, who is infected with HCMV or at risk for HCMV infection, with the purpose to cure, heal, alleviate, relieve, alter, remedy, ameliorate, improve, or affect the infection, the symptoms of the infection, or the predisposition toward the infection. "An effective amount" as used herein refers to the amount of each active agent which, upon administration with one or more other active agents to a subject in need thereof, is required to confer therapeutic effect on the subject. Effective amounts vary, as recognized by those skilled in the art, depending on route of administration, excipient usage, and the co-usage with other active agents.

Conventional methods, known to those of ordinary skill in the art of medicine, can be used to administer an antibody of this invention or its encoding nucleic acid(s) to a subject. For example, the antibody or the nucleic acid(s) can be administered via intravenous or subcutaneous injection, or via injectable depot routes of administration such as using 1-, 3-, or 6-month depot injectable or biodegradable materials and methods.

In another example, the nucleic acid(s) is delivered via a live vector, such as *Salmonella*, BCG, adenovirus, poxvirus or vaccinia.

Injectable compositions containing either the antibody or its encoding nucleic acid(s) may contain various carriers such as vegetable oils, dimethylactamide, dimethylformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Isolation of Human Anti-HCMV scFv Antibodies from a Mixed Phage scFv Library

A scFv phage display library was generated using RNAs isolated from 50 healthy Asian adults, following the procedure described in Clackson et al., *Nature*, 352:624-628 (1991). Briefly, mRNAs were purified from B lymphocytes isolated from the 50 healthy Asian adults. cDNAs corresponding to the $V_H$ domains of immunoglobulin proteins were amplified from these mRNAs via RT-PCR, using the following primers:

$V_H$ back:
HuVH1abacksfi:
(SEQ ID NO: 7)
5'-GTCCTCGCAACTGCGGCCCAGCCGGCCATGGCCCAGGTGCAGCTGGT
GSARTCTGG-3'

HuVH2abacksfi:
(SEQ ID NO: 8)
5'-GTCCTCGCAACTGCGGCCCAGCCGGCCATGGCCCAGGTCAACTTAAG
GGAGTCTGG-3'

HuVH3abacksfi:
(SEQ ID NO: 9)
5'-GTCCTCGCAACTGCGGCCCAGCCGGCCATGGCCGAGGTGCAGCTGKT
GGAGWCY-3'

HuVH4abacksfi:
(SEQ ID NO: 10)
5'-GTCCTCGCAACTGCGGCCCAGCCGGCCATGGCCCAGGTGCAGCTGCA
GGAGTCSG-3'

HuVH5abacksfi:
(SEQ ID NO: 11)
5'-GTCCTCGCAACTGCGGCCCAGCCGGCCATGGCCGAGGTGCAGCTGTT
GCAGTCTGC-3'

HuVH6abacksfi:
(SEQ ID NO: 12)
5'-GTCCTCGCAACTGCGGCCCAGCCGGCCATGGCCCAGGTACAGCTGCA
GCAGTCA-3'

HuVH14abacksfi:
(SEQ ID NO: 13)
5'-GTCCTCGCAACTGCGGCCCAGCCGGCCATGGCCCAGRTCACCTTGAA
GGAGTCTG-3'

HuVH16abacksfi:
(SEQ ID NO: 14)
5'-GTCCTCGCAACTGCGGCCCAGCCGGCCATGGCCCAGGTGCAGCTACA
GCAGTGGG-3'

$J_H$ for:
HuJH1-2 for:
(SEQ ID NO: 15)
5'-TGAGGAGACGGTGACCAGGGTGCC-3'

HuJH3 for:
(SEQ ID NO: 16)
5'-TGAAGAGACGGTGACCATTGTCCC-3'

HuJH4-5 for:
(SEQ ID NO: 17)
5'-TGAGGAGACGGTGACCAGGGTTCC-3'

HuJH6 for:
(SEQ ID NO: 18)
5'-TGAGGAGACGGTGACCGTGGTCCC-3' cDNAs corresponding to the $V_L$ domains of immunoglobulins were amplified using the primers shown below.

$V_K$ back:
HuVK1a back:
(SEQ ID NO: 19)
5'-GACATCCAGATGACCCAGTCTCC-3'

HuVK2a back:
(SEQ ID NO: 20)
5'-GATGTTGTGATGACTCAGTCTCC-3'

HuVK3a back"
(SEQ ID NO: 21)
5'-GAAATTGTGTTGACGCAGTCTCC-3'

HuVK4a back:
(SEQ ID NO: 22)
5'-GACATCGTGATGACCCAGTCTCC-3'

HuVK5a back:
(SEQ ID NO: 23)
5'-GAAACGACACTCACGCAGTCTCC-3'

HuVK6a back:
(SEQ ID NO: 24)
5'-GAAATTGTGCTGACTCAGTCTCC-3'

$J_K$ for Not:
HuJK1forNot:
(SEQ ID NO: 25)
5'-GAGTCATTCTCGACTTGCGGCCGCACGTTTGATTTCCACCTTGGTC
CC-3'

HuJK2forNot:
(SEQ ID NO: 26)
5'-GAGTCATTCTCGACTTGCGGCCGCACGTTTGATCTCCAGCTTGGTCC
C-3'

HuJK3forNot:
(SEQ ID NO: 27)
5'-GAGTCATTCTCGACTTGCGGCCGCACGTTTGATATCCACTTTGGTCC
C-3'

HuJK4forNot:
(SEQ ID NO: 28)
5'-GAGTCATTCTCGACTTGCGGCCGCACGTTTGATCTCCACCTTGGTCC
C-3'

HuJK5forNot:
(SEQ ID NO: 29)
5'-GAGTCATTCTCGACTTGCGGCCGCACGTTTAATCTCCAGTCGTGTCC
C-3'

$V_\lambda$ back:
HuVL1 back:
(SEQ ID NO: 30)
5'-CAGTCTGTGTTGACGCAGCCGCC-3'

-continued

HuVL2 back:
(SEQ ID NO: 31)
5'-CAGTCTGCCCTGACTCAGCCTGC-3'

HuVL3a back:
(SEQ ID NO: 32)
5'-TCCTATGTGCTGACTCAGCCACC-3'

HuVL3b back:
(SEQ ID NO: 33)
5'-TCTTCTGAGCTGACTCAGGACCC-3'

HuVL4 back:
(SEQ ID NO: 34)
5'-CACGTTATACTGACTCAACCGCC-3'

HuVL5 back:
(SEQ ID NO: 35)
5'-CAGGCTGTGCTCACTCAGCCGTC-3'

HuVL6 back:
(SEQ ID NO: 36)
5'-AATTTTATGCTGACTCAGCCCCA-3'

$J_\lambda$ for Not:
HuJL1forNot:
(SEQ ID NO: 37)
5'-GAGTCATTCTCGACTTGCGGCCGCACCTAGGACGGTGACCTTGGT C
CC-3'

HuJL2-3forNot:
(SEQ ID NO: 38)
5'-GAGTCATTCTCGACTTGCGGCCGCACCTAGGACGGTCAGCTTGGT C
CC-3'

HuJL4-5forNot:
(SEQ ID NO: 39)
5'-GAGTCATTCTCGACTTGCGGCCGCACCTAAAACGGTGAGCTGGGT C
CC-3'

The $V_H$ cDNAs were then randomly linked, by PCR reactions, with the $V_L$ cDNAs via a linker having the nucleotide sequence of 5'-GGTGGAGGCGGTTCAGGCGGAGGTG-GCTCT GGCGGTGGCGGATCG-3' (SEQ ID NO:40) to form fragments encoding scFv antibodies. These fragments were cloned into pCANTAB 5E phagemid vector to produce the scFv phage display library.

Three additional scFv phage display libraries were constructed using mRNAs isolated from B lymphocytes of an Indian patient, B lymphocytes of a patient having severe acute respiratory syndrome, and spleen cells of a Taiwanese patient, following the procedures described above. These three libraries were combined with the library described above to form a mixed scFv phage display library, which was used to screen for anti-HCMV scFv antibodies. This mixed library has a phage titer of $1 \times 10^{13}$ pfU/ml.

The just-described mixed phage library was subjected to screening for clones that express scFv antibodies specific to HCMV as follows.

First, phages displaying anti-HCMV antibodies were enriched by three rounds of bio-panning as described below. An immunotube was coated with HCMV RC256 particles diluted in coating buffer (50 mM sodium bicarbonate, PH9.6, $5 \times 10^5$/ml) at 4° C. overnight, washed three times with PBS containing 0.1% Tween, blocked with PBS containing 2% non-fat milk, and again washed three times with PBS containing 0.1% Tween. An aliquot of the mixed library was diluted in PBS containing 2% non-fat milk, and added to the immunotube coated with HCMV. After a two-hour incubation, the immunotube was washed 10 times with PBS containing 0.1% Tween and then 10 times with PBS to remove unbound phages. Eluted phage by adding 100 mM triethylaine and neutralized with 1M Tris, PH7.4. The eluted-phage infected TG1 bacteria and incubated at 37° C. for 30 minutes. Plated the infected-TG1 on 2YT/ampicillin/glucose plate and grew at 30° C. overnight. Added 2YT/ampicillin/glucose/15% glycerol to plate and loosen the cells with a glass spreader. Inoculated scraped bacteria to 2YT/ampicillin/glucose and cultured at 37° C., 250 rpm until O.D. 600 is 0.5. After addition of $5 \times 10^{10}$ pfu of M13KO7 helper phage were added to the cell culture, which was incubated at 37° C., for 30 minutes. The cell culture was then centrifuged at 2,000×g for 10 minutes at room temperature. The cell pellet thus formed was resuspended in 10 ml 2×YT containing ampicillin and kanamycin, and incubated at 30° C., 250 rpm overnight. The culture was centrifuged at 10,000 g for 20 minutes at 4° C. to collect the resultant supernatant. PEG/NaCl was then added to the supernatant. After an hour, the supernatant was centrifuged to collect the resultant pellet, which was resuspend in PBS and centrifuged to remove most of the remaining bacterial debris. The PBS-phages thus formed was the $1^{st}$ round enriched scFv phage library.

An aliquot of this $1^{st}$ round enriched library was subjected to the second round, and then third round, bio-panning to generate a $3^{rd}$ round enriched phage library (in TG1 cells) following the same procedures described above, except that the HCMV-coated immunotube, after being incubated with the phages, was washed 20 times with PBS containing 0.1% Tween-20 and 20 times with PBS.

Second, the $3^{rd}$ round enriched phage library was subjected to ELISA screening as follows. An aliquot of the $3^{rd}$ round enriched phage library (in TG1 cells) was diluted and plated on 2×YT/ampicillin/glucose for single colonies and incubated at 37° C. overnight. 188 single colonies each were inoculated separately in 2×YT/ampicillin/glucose and incubated at 37° C., 250 rpm overnight. An aliquot of the culture thus formed was inoculated into a fresh 2×YT/ampicillin/glucose medium containing $10^9$ pfu M13KO7helper phage, cultured at 37° C., 250 rpm for 1-2 hours, and then centrifuged at 14,000 rpm for 5 minutes at room temperature. The cell pellet thus formed was suspended in 2×YT/ampicillin/kanamycin, incubated at 30° C., 250 rpm overnight, and then centrifuged at 2000 g for 30 minutes at room temperature. The supernatant was subjected to the ELISA screening as follows.

A test multi-well microplate was coated with HCMV RC256 and a control microplate was coated with lysate of *E. coli* cells transfected with vector pET-22b. Phages prepared from each of the 188 colonies as described above were added to one well in the test microplate and one well in the control microplate. Both microplates were incubated at room temperature for 2 hours, and washed three times with PBS containing 0.05% Tween. HRP-conjugated anti-M13 antibodies, diluted in PBS containing 0.05% Tween and 2% non-fat milk, were then added to both microplates, which were incubated at room temperature for 1 hour. The microplates were again washed three times with PBS containing 0.05% Tween, and HRP substrates were then added therein. The microplates were then incubated at room temperature until a blue color was developed. $O.D._{450}$ and $O.D._{650}$ of each well were determined using an ELISA reader.

48 phage clones were found positive (HCMV/control>8) in the ELISA screening described above. cDNAs encoding scFv expressed therein were amplified from these clones and their nucleotide sequences were determined. One of the positive phage clones express HCMV-20 scFv antibody (SEQ ID NO:3).

EXAMPLE 2

Preparation of HCMV-20 scFv Antibody

The cDNA encoding HCMV-20 scFv Antibody was cloned into pET27b(+) expression vector, which was then transfected into *E. coli*. A positive *E. coli* clone was incubated overnight at 37° C. in a LB/kanamycin medium. 70 ml of this overnight culture was inoculated into a fresh LB/kanamycin medium and cultured for 2 hours at 37° C. IPTG was then added to the culture to a final concentration of 1 mM and the culture was further cultivated at 30° C. for 5 hours. *E. coli* cells were then harvested via centrifugation, resuspended in Buffer A (50 mM sodium phosphate, 1M sodium chloride, PH8.0), lysated by a microfludizer, and centrifuged again at 14,000 rpm for 20 minutes at 4° C. to form a supernatant that contains HCMV-20 scFv, expressed as a His-tag fused polypeptide. This fusion protein was purified via affinity column chromatography following conventional methods. The protein thus purified was then subjected to polyacrylamide gel electrophoresis to determine its purity and quantity.

EXAMPLE 3

Neutralization of HCMV with HCMV-20 scFv Antibody

Plaque reduction assay was applied to test the ability of HCMV-20 scFv antibody for neutralizing HCMV infection. Briefly, $1\times10^5$ MRC-5 cells were seeded in each well of a 24-well plate and cultured in MEM medium at 37° C. overnight. The medium was then replaced with a mixture (1 ml/well) containing 1×PBS, MEM (FBS free), HCMV-20, and HCMV RC256 ($1\times10^3$ pfu/ml). Before placing in the plate, the mixture was pre-cultured at 37° C. for one hour. An unrelated scFv antibody, globH 6, was used as a negative control. The plate, containing the mixture, was incubated at 37° C. for 2 hr and the mixture was then removed. The plate was washed with 1×PBS once; 0.4% agarose in MEM containing 10% FBS was then added therein. After the agarose was solidified, the plate was placed in a 37° C. incubator for 7 days. During this period, 500 μl MEM containing 10% FBS were added to each well in the plate. At day 8, MEM was removed from the plate, and 500 μl 1×PBS/methanol (1:1 by volume) was then added in each well in the plate. Five minutes later, the 1×PBS/methanol was replaced with 500 μl 100% methanol to fix the cells contained in the wells. After another 5 min, the methanol was removed and the cells were stained with 250 μl crystal violet for 10 min. The crystal violet was then washed with water from the plate, which was then air dried. The numbers of plaques contained in each well in the plate were then counted under a microscope.

As shown in Tables 1 and 2 below, HCMV-20 significantly reduced plaque formation rate in MRC5 cells infected with HCMV RC256. On the contrary, globH 6, the control antibody, failed to suppress plaque formation.

TABLE 1

Plaque Numbers in MRC5 Cells Infected with HCMV RC256 in the Presence or Absence of HCMV-20 scFv antibody

| HCMV 20 | cell only | 16.3 uM | 8.1 uM | 4.1 uM | 2.0 uM | 1.0 uM | virus only |
|---|---|---|---|---|---|---|---|
| Test 1 | 0 | 15 | 20 | 23 | 36 | 92 | 152 |
| Test 2 | 0 | 16 | 16 | 17 | 42 | 93 | 139 |

TABLE 2

Plaque Numbers in MRC5 Cells Infected with HCMV RC256 in the Presence or Absence of globH 6 antibody

| globH 6 | cell only | 8.1 uM | 4.1 uM | 2.0 uM | 1.0 uM | virus only |
|---|---|---|---|---|---|---|
| Test 1 | 0 | 60 | 62 | 61 | 85 | 69 |
| Test 2 | 0 | 63 | 61 | 82 | 88 | 85 |

Other Embodiments

All of the features disclosed in this specification may be combined in any combination.

Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated antibody specifically binding to human cytomegalovirus, wherein the antibody contains a heavy chain variable region ($V_H$) including an amino acid sequence at least 95% identical to SEQ ID NO:1, and a light chain variable region ($V_L$) including an amino acid sequence at least 95% identical to SEQ ID NO:2.

2. The antibody of claim 1, wherein the antibody contains a $V_H$ including the amino acid sequence of SEQ ID NO:1 or a $V_L$ including the amino acid sequence of SEQ ID NO:2.

3. The antibody of claim 2, wherein the antibody contains a polypeptide including the amino acid sequence of SEQ ID NO:3.

4. A pharmaceutical composition comprising the antibody of claim 1 and a pharmaceutically acceptable carrier.

5. A method for treating cytomegalovirus infection, comprising administering to a subject in need thereof an effective amount of an antibody that specifically binds to human cytomegalovirus, wherein the antibody contains a $V_H$ including an amino acid sequence at least 95% identical to SEQ ID NO:1, and a $V_L$ including an amino acid sequence at least 95% identical to SEQ ID NO:2.

6. The method of claim 5, wherein the antibody contains a polypeptide including the amino acid sequence of SEQ ID NO:3.

7. The pharmaceutical composition of claim 4, wherein the antibody contains a $V_H$ including the amino acid sequence of SEQ ID NO:1 or a $V_L$ including the amino acid sequence of SEQ ID NO:2.

8. The pharmaceutical composition of claim 7, wherein the antibody contains a polypeptide including the amino acid sequence of SEQ ID NO:3.

9. The method of claim 5, wherein the antibody contains a $V_H$ including the amino acid sequence of SEQ ID NO:1 or a $V_L$ including the amino acid sequence of SEQ ID NO:2.

10. An isolated antibody specifically binding to human cytomegalovirus, wherein the antibody contains a heavy chain variable region ($V_H$) including the same complementarity determinant regions (CDRs) as those in SEQ ID NO:1 and a light chain variable region ($V_L$) including the same CDRs as those in SEQ ID NO:2.

11. A pharmaceutical composition containing the antibody of claim 10 and a pharmaceutically acceptable carrier.

12. A method for treating cytomegalovirus infection, comprising administering to a subject in need thereof an effective amount of the antibody of claim 10.

* * * * *